United States Patent
Sugo et al.

[11] Patent Number: 6,011,989
[45] Date of Patent: Jan. 4, 2000

[54] PATIENT MONITORING APPARATUS

[75] Inventors: Yoshihiro Sugo; Takeshi Sohma; Rie Tanaka; Wenxi Chen; Shigeru Aso; Ryoichi Ochiai, all of Tokyo, Japan

[73] Assignee: Nihon Kohden Corporation, Tokyo, Japan

[21] Appl. No.: 09/129,213

[22] Filed: Aug. 5, 1998

[30] Foreign Application Priority Data

Aug. 5, 1997 [JP] Japan .................................. 9-210292

[51] Int. Cl.$^7$ ...................................................... A61B 5/02
[52] U.S. Cl. ............................................................. 600/513
[58] Field of Search ................................................ 600/513

[56] References Cited

U.S. PATENT DOCUMENTS

| | | | |
|---|---|---|---|
| 5,033,472 | 7/1991 | Sato et al ............................. | 600/513 |
| 5,339,822 | 8/1994 | Taylor et al. ........................... | 600/513 |
| 5,544,661 | 8/1996 | Davis et al. ............................ | 600/513 |

*Primary Examiner*—William E. Kamm
*Attorney, Agent, or Firm*—Sughrue, Mion, Zinn, Macpeak & Seas, PLLC

[57] ABSTRACT

An electrocardiogram signal derived from electrocardiogram measuring means 1 and a pulse signal derived from pulse-wave measuring means 2 are applied to a CPU 30. The CPU 30 processes the cardiogram signal to detect a QRS wave signal, and processes the pulse signal to detect the amplitude of the pulse signal. The CPU 30 judges whether or not the QRS wave is caused by a ventricular premature contraction. If two QRS waves, not caused by ventricular premature contraction, occurs successively, and the CPU 30 judges if $A0 \times k > A1$. The CPU 30 judges that a supraventricular extrasystole is occurred. Here, A0 is an amplitude of the first QSR wave; A1 is an amplitude of the second QSR wave; and k is a preset value, $0 < k < 1$.

3 Claims, 3 Drawing Sheets

PATIENT MONITORING APPARATUS

BACKGROUND OF THE INVENTION

1. Field of the Invention

The present invention relates to an apparatus for non-invasively monitoring a supraventricular extrasystole as one of state changes of the excitation conducting system of the heat by use of electrocardiogram information and pulse-wave information.

2. Related art

The non-invasive monitoring apparatus uses mainly the information of electrocardiograms, arterial oxygen saturation, blood pressure measured by the oscillometric blood-pressure measuring apparatus and the like as parameters representative of dynamic states of a patient. Of those parameters, electrocardiogram information, arterial oxygen saturation and the like may continuously be measured. In particular the electrocardiogram information is used as a parameter sensitively representing a change of a dynamic state of the patient.

Thus, the electrocardiogram information has been used as the continuously monitoring parameter. An arrhythmia of the patient is monitored by use of the waveforms and heat rate on the electrocardiogram. The monitoring based on only the electrocardiogram has the following problems.

A supraventricular extrasystole, if it frequently occurs, indicates a symptom of a disease of the atrium or a premonitary symptom of the atrial fibrillation. Because of this, it must be detected. In detecting the supraventricular extrasystole, one will encounter the following difficulties. A QRS wave caused by the normal sinus rhythm contraction as a normal contraction is the same as by the supraventricular extrasystole. Therefore, it is impossible to discriminate between the normal sinus rhythm contraction and the supraventricular extrasystole by use of the QRS wave alone. The supraventricular extrasystole does not always appear as a clear variation of the R—R interval (R-wave to R wave interval). Therefore, it is often difficult to discriminate between the R—R interval variation by the supraventricular extrasystole and that by breathing. A discrimination between the normal sinus rhythm contraction and the supraventricular extrasystole may be made on the basis of a waveshape of the P wave. The signal level of the P wave is small. Therefore, the P wave sometimes sinks into the preceding T wave. The waveshape of the P wave varies depending on a location where the extrasystole takes place. For this reason, it is difficult to discriminate between the sinus rhythm contraction and the supraventricular extrasystole.

Thus, it is difficult to detect the supraventricular extrasystole using only the electrocardiogram information for the parameter continuously obtained in non-invasive manner.

SUMMARY OF THE INVENTION

Accordingly, an object of the present invention is to monitor the supraventricular extrasystole in non-invasive manner.

A first aspect of the preset invention, a patient monitoring apparatus comprising: electrocardiogram measuring means for measuring electrocardiograms; pulse-wave measuring means for measuring pulse waves; QRS-wave detecting means for detecting QRS waves on an electrocardiogram measured by the electrocardiogram measuring means; pulse-amplitude detecting means for detecting amplitudes of pulse waves measured by the pulse-wave measuring means; first judging means for judging whether or not the QRS wave measured by QRS-wave detecting means is caused by a ventricular premature contraction; and second judging means for operating such that if the first judging means judges that the QRS wave is not the QRS wave caused by a ventricular premature contraction, the second judging means judges whether or not the amplitude of the pulse wave corresponding to the QRS wave detected by pulse-amplitude detecting means is smaller than a preset value.

With such an arrangement, the first judging means removes the QRS wave caused by the ventricular premature contraction, and the second judging means judges whether or not the amplitude of the pulse wave corresponding to the QRS wave which is not the QRS wave caused by the ventricular premature contraction is smaller than a preset value.

In the patient monitoring apparatus of the present invention, the second judging means includes third judging means for judging whether or not at least two QRS waves, which are those not caused by the ventricular premature contraction, appear in successive fashion; and fourth judging means operating such that if the third judging means judges that at least two QRS waves which are those not caused by the ventricular permature contraction successively appear, the fourth judging means judges whether or not the amplitude of the pulse wave corresponding to the second QRS wave is smaller than a value set up on the basis of the amplitude of the pulse wave corresponding to the first QRS wave.

When two QRS waves, which are those not caused by the ventricular premature contraction, appear in successive fashion, the fourth judging means judges whether or not the amplitude of the pulse wave corresponding to the second QRS wave is smaller than a value set up on the basis of the amplitude of the pulse wave corresponding to the first QRS wave.

DETAILED DESCRIPTION OF THE PREFERRED EMBODIMENTS

Figure 1:
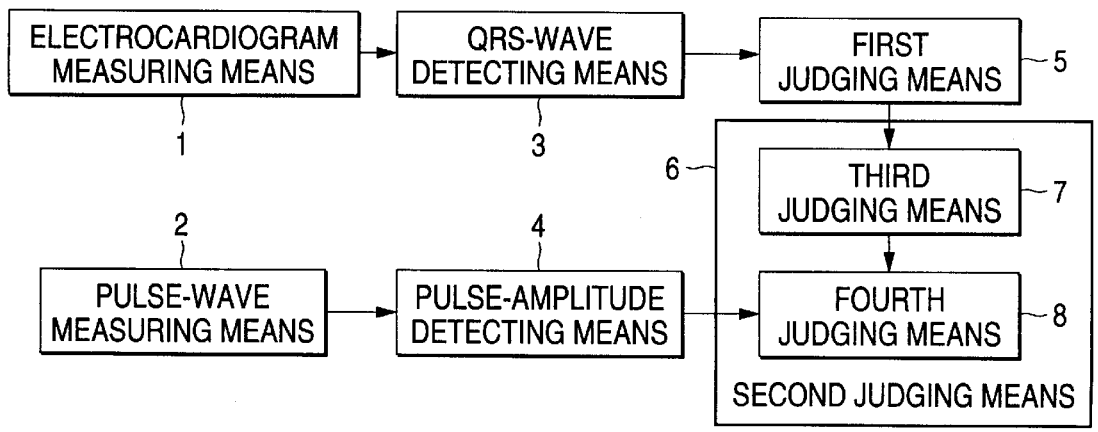
FIG. 1 is a block diagram showing the conceptual arrangement of a patient monitoring apparatus constructed according to the present invention.

A first embodiment of the present invention will be described. The embodiment is a patient monitoring apparatus for detecting a supraventricular extrasystole of the heart. The patient monitoring apparatus is generally made up of electrocardiogram measuring means 1, pulse-wave measuring means 2 for measuring a pulse wave, QRS-wave detecting means 3 for measuring a QRS wave on an electrocardiogram measured by the electrocardiogram measuring means 1, pulse-amplitude detecting means 4 for detecting an amplitude of a pulse wave measured by the pulse-wave measuring means 2, first judging means 5 for judging as to whether or not a QRS wave detected by the QRS-wave detecting means 3 is a wave produced by the ventricular premature contraction (VPC), and second judging means 6 for judging as to whether or not a ratio of amplitudes of a pulse wave detected by the pulse-amplitude detecting means 4 is larger or smaller than a preset value, the detected pulse wave corresponding to the QRS wave, which is judged to be not the wave produced by the VPC. The second judging means 6 includes third judging means 7 and fourth judging means 8. The third judging means 7 judges as to whether or not two QRS waves not by the VPC have appeared in succession. The fourth judging means 8 operates such that when the third judging means 7 judges that two QRS waves have successively appeared, the fourth judging means 8 judges whether or not the amplitude of the pulse wave corresponding to the second QRS wave of those successive ones is smaller than a value set on the basis of the amplitude of the pulse wave corresponding to the first QRS wave of the successive ones (in the specification, the first QRS wave appears earlier than the second one).

Figure 2:
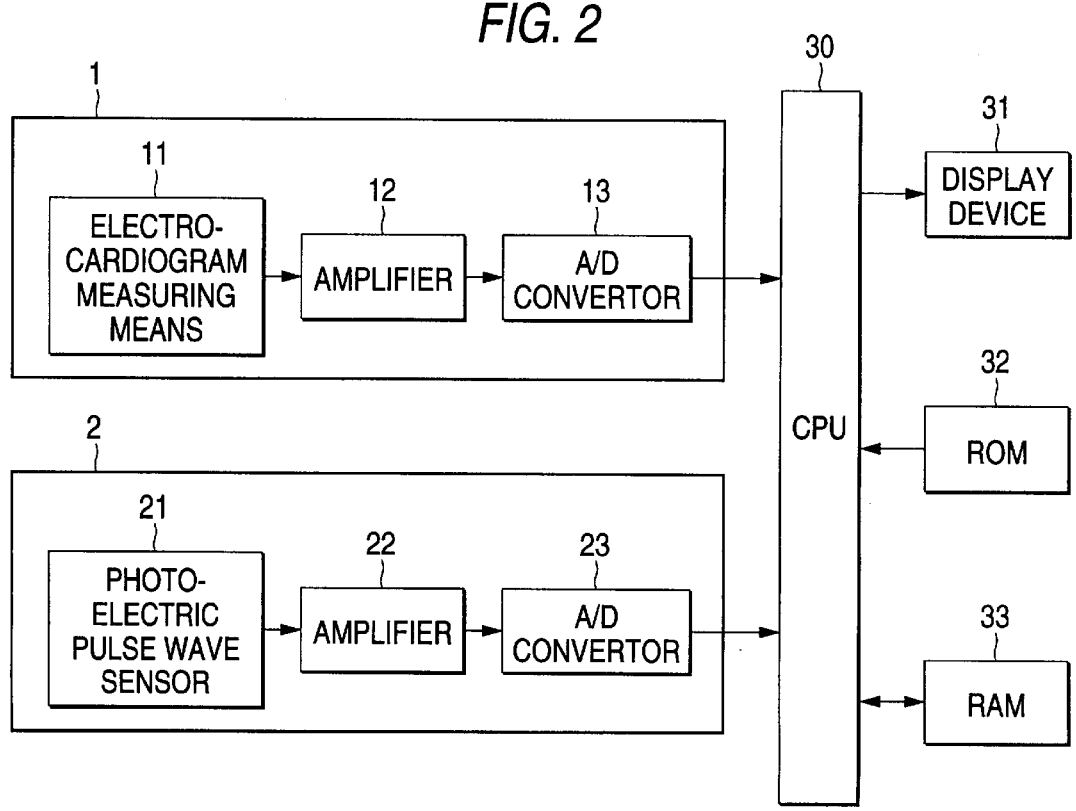
FIG. 2 is a block diagram showing a hardware arrangement of the patient monitoring apparatus of FIG. 1.

An arrangement of the detail of the patient monitoring apparatus is shown in FIG. 2. The electrocardiogram measuring means 1 includes an electrocardiogram electrode 11 to be placed on the chest of a patient, an amplifier 12 for amplifying a cardiogram signal derived from the electrocardiogram electrode 11, and an A/D converter 13 for converting the amplified cardiogram signal into a digital signal. The pulse-wave measuring means 2 includes a photoelectric pulse wave sensor 21 put on the finger tip of the patient, an amplifier 22 for amplifying a pulse wave signal derived from the photoelectric pulse wave sensor 21, and an A/D converter 23 for amplifying the amplified pulse wave signal into a digital signal. The output signals of the A/D converter 13 and the A/D converter 23 are input to a CPU 30.

The CPU 30 is connected to a display device 31, a ROM 32 and a RAM 33. The CPU 30 receives a cardiogram signal from the electrocardiogram measuring means 1 and a pulse wave signal from the pulse-wave measuring means 2, processes those signals in predetermined rules, and displays the result of the processing on the display device 31. The ROM 32 stores programs for the process carried out by the CPU 30, and data used for the processing. The RAM 33 is used such that when the CPU 30 executes the process, writes necessary data into the RAM 33 and reads out necessary data. A part of the contents of the RAM 33 contains registers A1 and A0, and flags F1, F2 and F3: register A1 contains the amplitude of the pulse wave corresponding to the previous QRS wave; register A0 contains the amplitude of the pulse wave corresponding to the QRS wave appearing two waves before the present one; flag F1 indicates whether or not the present QRS wave is due to the ventricular premature contraction (VPC); flag F2 indicates whether or not the previous QRS wave is due to the VPC; and flag F3 indicates the QRS wave appearing two waves earlier than the present one.

If the QRS wave is due to the VPC, the corresponding flags F1 to F3 are set to "0", and if it is not due to the VPC, those corresponding flags are set to "1".

Figures 3, 4:
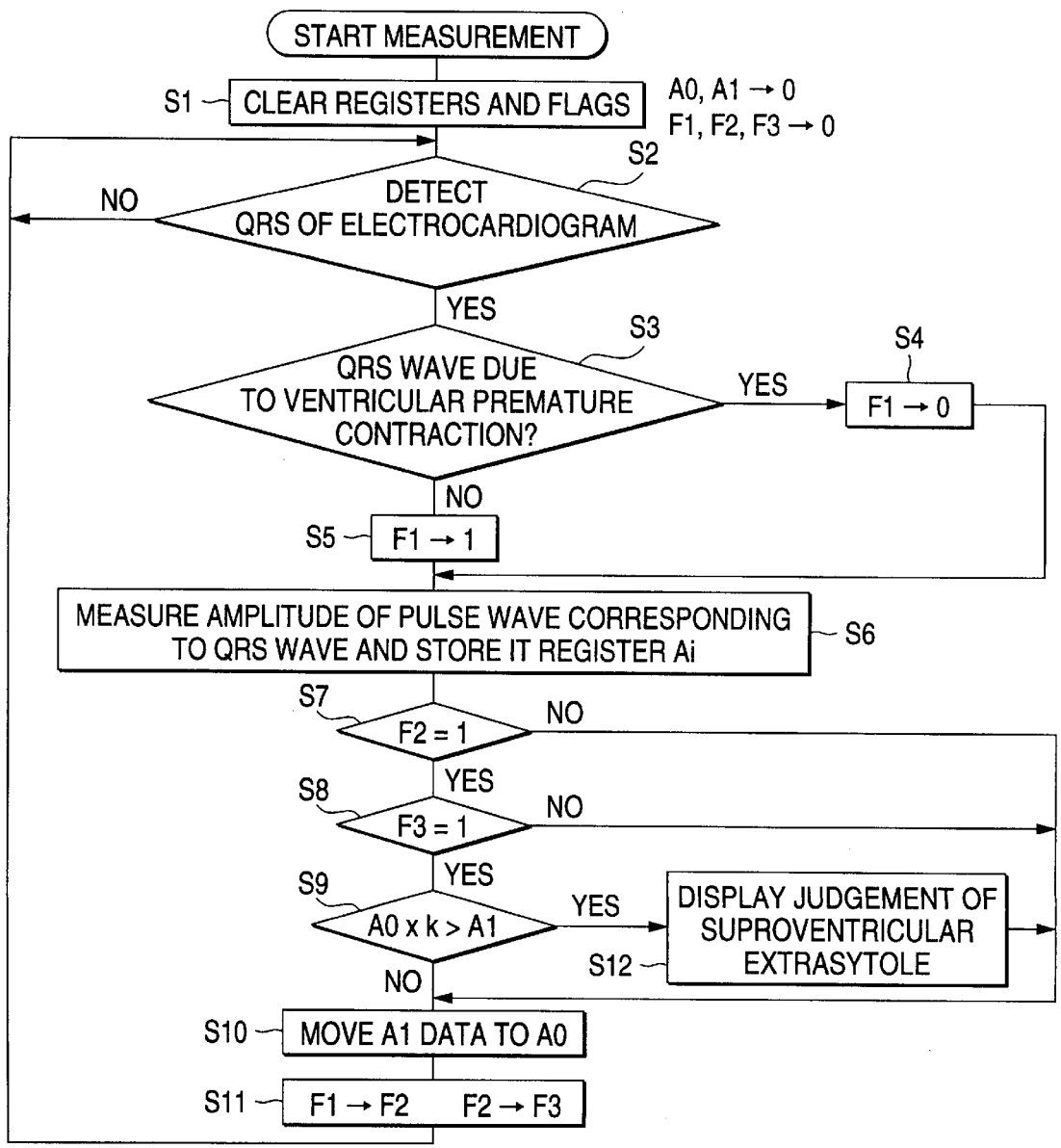
FIG. 3 is a diagram showing the contents of a RAM 33 in the FIG. 2 arrangement.
FIG. 4 is a flow chart showing an operation of the patient monitoring apparatus shown in FIGS. 1 and 2.
Figure 5:
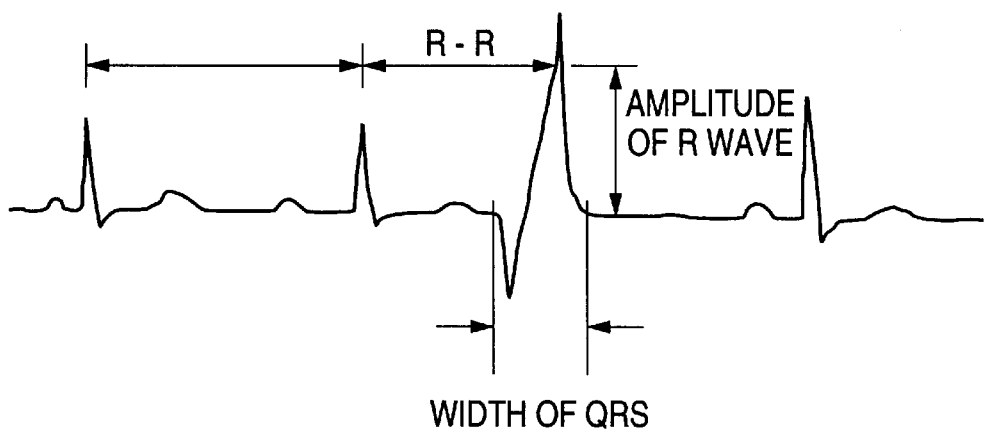
FIG. 5 is a waveform diagram showing the waveforms of an electrocardiogram, when include normal wave and ventricular premature contraction wave.

An operation of the thus constructed patient monitoring apparatus will be described with reference to a flow chart of FIG. 4. To start a measurement, the CPU 30 clears the registers and the flags (step S1); waits till a QRS wave at preset of a cardiogram signal derived from the electrocardiogram measuring means 1 appears (step S2); and if it detects the QRS wave, it judges whether or not the QRS wave is due to the ventricular premature contraction (VPC) (step S3). This judgement is made by use of the results of detecting a variation R—R interval (R wave to R wave interval), a variation of the amplitude of the R wave and the width (broadened) of the QRS wave.

In a step S3, if the QRS wave that is detected this time is due to the VPC, the CPU 30 resets the flag F1 to "0" (step S4), and advances to a step S6. If the QRS wave is not due to the VPC in the step S3, the CPU 30 sets the flag F1 to "1" (step S5), and advances to a step S6. In the step S6, the CPU 30 measures an amplitude of the pulse wave corresponding to the QRS wave, and loads the measured amplitude into the register A1. In a step S7, the CPU 30 judges whether or not the QRS wave previously detected is due to the VPC, viz., F2=1. If the answer is YES, the CPU 30 judges whether or not the QRS wave detected two waves before the present one, viz., F2=1. If the answer is YES, the CPU 30 executes a step S9. In this step, it compares an amplitude of the pulse wave corresponding to the QRS wave previously detected with that of the pulse wave corresponding to the QRS wave detected two waves before the present one. In other words, the CPU 30 judges if A0×k>A1 (A0: the amplitude value stored in the register A0, k is a preset value, 0<k<1, A1: the amplitude value stored in the register A1).

Figure 6:
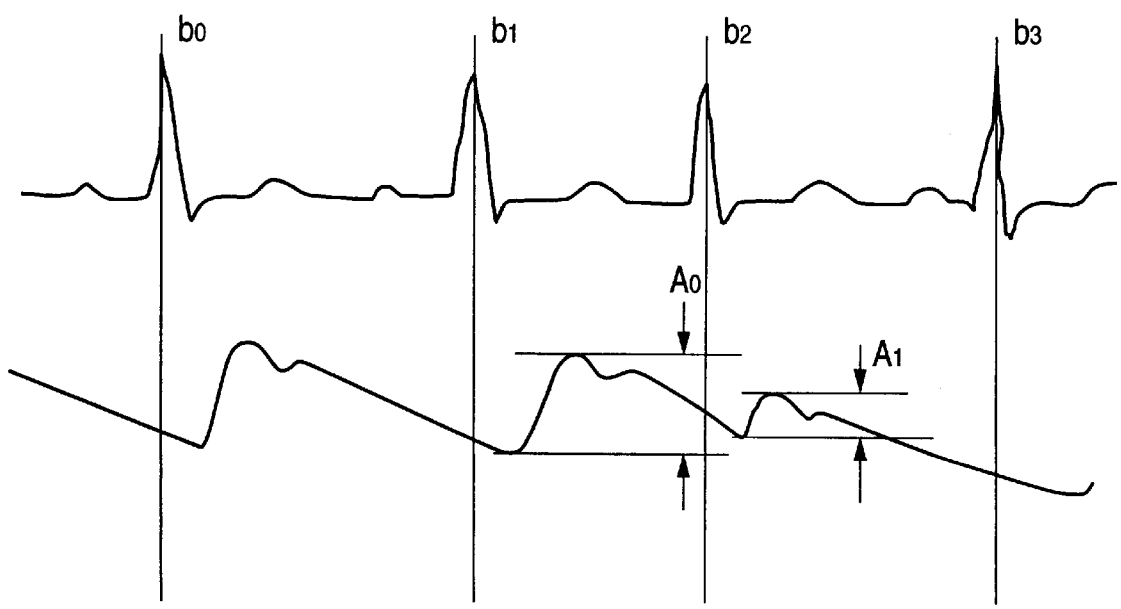
FIG. 6 is a waveform diagram showing the waveforms of an electrocardiogram and a pulse signal, which are to be processed by the FIGS. 1 and 2 apparatus.

FIG. 6 diagrammatically shows examples of the amplitude value A1 of the pulse wave corresponding to the QRS wave previously detected, and the amplitude value A0 of the pulse wave corresponding to the QRS wave detected two waves earlier than the present one.

In the figure, b3 is the QRS wave at present; b2 is the QRS wave previously detected; and b1 is the QRS wave detected two waves before the present one.

If A0×k>A1 (step S9), the CPU 30 judges that the supraventricular extrasystole takes place, and displays that the supraventricular extrasystole takes place on the screen of the display device 31 (step S12), and goes to a step S10. In this step, the CPU 30 shifts the data from the register A1 to the register A0. If the flag F2 is not "1", the CPU 30 advances to a step S10 when F3 is not "1" in the step S8 and also when A0×k>A1 is not satisfied in the step S9. After processing the step S9, the CPU 30 goes to a step S11. In this step, the CPU 30 writes the contents of the flag F1 into the flag F2, and the contents of the flag F2 into the flag F3, and returns to the step S2.

As described above, the CPU 30 first checks if the VPC takes place; if the VPC does not take place, it checks if the amplitude of the pulse wave drops; and detects that the supraventricular extrasystole takes place. The reason why the above process is used will be described hereinafter.

When the systole not attendant with an active contraction of the atrium, such as the supraventricular extrasystole, is compared with the sinus rhythm contraction, the cardiac output per one heart beat in the former is smaller than in the latter under the condition of the equal heart rates. Some reports describe that the cardiac output in the former is 80% or smaller than in the latter (see Resnekov L. Circulatory Effects of Cardiac Dysrhthmias. Cardiovascular Clinics, Vol. 2, No. 2, p23, 1970). A variation of the cardiac output is substantially proportional to a variation of the amplitude of the pulse wave. This fact entails that a supraventricular extrasystole may be detected by detecting a decrease of the amplitude of the pulse wave. When the R—R interval is reduced and hence the filling of the heat with blood is not sufficient, the amplitude of the pulse wave is further reduced. Also in the case of the VPC (ventricular premature contraction), the pulse wave amplitude decreases. Therefore, the use of only the amplitude reduction of the pulse wave fails to discriminate the supraventricular extrasystole and the VPC (ventricular premature contraction). To cope with this, the present invention removes the QRS wave caused by the VPC in advance, and observes the pulse wave corresponding to the QRS wave left after the removal of the VPC basis QRS wave. The VPC can be recognized from the cardiogram, as already stated.

The patient monitoring apparatus of the present invention measures the two successive pulse waves, or the first and second pulse waves, and detects a state that the amplitude of the second pulse wave decreases to a predetermined percentage or larger of that of the first pulse wave. Therefore, an invariable detecting accuracy of the pulse amplitude detection is secured for all the patients.

The correspondence of the processing functions of the CPU 30 (FIG. 4) and the blocks of the FIG. 1 diagram is as follows: the processing of the step S2 (FIG. 4) corresponds to the QRS-wave detecting means 3 (FIG. 1); the processing of the step S6 (FIG. 4) corresponds to the pulse amplitude detecting means 4 (FIG. 1); the processing of the step S3, to the first judging means 5; the processings of the steps S7, S8 and S9, to the second judging means 6; the processings of the steps S7 and S8, to the third judging means 7; and the processing of the step S9, to the fourth judging means 8.

In the embodiment, k in the step S9 is 0.8. Also in the embodiment, if the systole is the supraventricular extrasystole, the information of that meaning is displayed. The same information may be presented by an alarm sound.

in the embodiment mentioned above, the patient monitoring apparatus is used for monitoring the supraventricular extrasystole. However, the patient monitoring apparatus, like the normal monitoring apparatus, is capable of displaying electrocardiograms and pulse wave signals by use of the display device 31. A no-invasive blood pressure measuring device may be attached to the patient monitoring apparatus of the invention. When the supraventricular extrasystole is measured, the blood pressure monitoring device is operated to quickly measure a blood pressure at that time.

The technical idea of the present invention enables the patient monitoring apparatus constructed incorporating the same thereinto to monitor the supraventricular extrasystole in a non-invasive manner.

In the patient monitoring apparatus of the present invention, the criterion in judging a decrease of the amplitude of the pulse wave is set up depending on the amplitude of the first pulse wave of the two successive ones. Therefore, an invariable detecting accuracy of the pulse amplitude detection is secured for all the patients.

What is claimed is:

1. A patient monitoring apparatus comprising:

electrocardiogram measuring means for measuring electrocardiograms;

pulse-wave measuring means for measuring pulse waves;

QRS-wave detecting means for detecting QRS waves on an electrocardiogram measured by said electrocardiogram measuring means;

pulse-amplitude detecting means for detecting amplitudes of pulse waves measured by said pulse-wave measuring means;

first judging means for judging whether or not the QRS wave measured by QRS-wave detecting means is caused by a specific arrhythmia; and second judging means for operating such that if said first judging means judges that the QRS wave is not the QRS wave caused by the specific arrhythmia, said second judging means judges whether or not the amplitude of the pulse wave corresponding to the QRS wave detected by pulse-amplitude detecting means is smaller than a preset value.

2. The patient monitoring apparatus according to claim 1, wherein the specific arrhythmia is a ventricular premature contraction.

3. The patient monitoring apparatus according to claim 1, in which said second judging means includes third judging means for judging whether or not at least two QRS waves, which are those not caused by the specific arrhythmia, appear in successive fashion; and fourth judging means for operating such that if said third judging means judges that at least two QRS waves which are those not caused by specific arrhythmia successively appear, said fourth judging means judges whether or not the amplitude of the pulse wave corresponding to the second QRS wave is smaller than a value set up on the basis of the amplitude of the pulse wave corresponding to the first QRS wave.

* * * * *